(12) United States Patent
Andersch

(10) Patent No.: US 10,016,358 B2
(45) Date of Patent: Jul. 10, 2018

(54) VAGINAL SUPPOSITORY COMPRISING LACTIC ACID

(71) Applicant: Bjorn Andersch, Saro (SE)

(72) Inventor: Bjorn Andersch, Saro (SE)

(73) Assignee: ROLF KULLGREN AB, Gnesta (SE)

(*) Notice: Subject to any disclaimer, the term of this patent is extended or adjusted under 35 U.S.C. 154(b) by 0 days.

(21) Appl. No.: 14/496,737

(22) Filed: Sep. 25, 2014

(65) Prior Publication Data

US 2015/0080467 A1    Mar. 19, 2015

Related U.S. Application Data

(62) Division of application No. 12/996,247, filed as application No. PCT/EP2009/056818 on Jun. 3, 2009, now Pat. No. 8,871,244.

(30) Foreign Application Priority Data

Jun. 4, 2008  (EP) .................................... 08157575

(51) Int. Cl.
| | | |
|---|---|---|
| A61K 9/00 | (2006.01) | |
| A61K 9/02 | (2006.01) | |
| A61K 31/19 | (2006.01) | |
| A61K 47/02 | (2006.01) | |
| A61K 47/34 | (2017.01) | |

(52) U.S. Cl.
CPC .............. *A61K 9/0034* (2013.01); *A61K 9/02* (2013.01); *A61K 31/19* (2013.01); *A61K 47/02* (2013.01); *A61K 47/34* (2013.01); *Y10S 514/967* (2013.01)

(58) Field of Classification Search
CPC ........ A61K 9/02; A61K 31/19; A61K 9/0034; Y10S 514/967
See application file for complete search history.

(56) References Cited

U.S. PATENT DOCUMENTS

| | | | | |
|---|---|---|---|---|
| 6,537,970 B1* | 3/2003 | Vulpescu | ............. | A61K 9/0034 514/25 |
| 6,740,333 B2* | 5/2004 | Beckett | ..................... | A61K 9/02 424/436 |
| 2007/0026074 A1* | 2/2007 | Martin | .................. | A61K 9/0034 424/488 |
| 2008/0161234 A1* | 7/2008 | Andersch | ............... | A61K 31/40 514/2.5 |

FOREIGN PATENT DOCUMENTS

| | | | | | |
|---|---|---|---|---|---|
| CA | 1109473 | A | * | 9/1981 | ........... C07D 221/18 |
| CN | 1972683 | A | | 5/2007 | |
| EP | 0257007 | A1 | * | 2/1988 | ........... A61K 9/0034 |
| EP | 0257007 | B1 | | 2/1988 | |
| EP | 1782794 | A2 | | 5/2007 | |
| HU | 224320 | B1 | * | 7/2005 | ............... A61K 9/02 |
| RO | 80931 | A | | 12/1980 | |
| WO | 2006/001766 | A1 | | 1/2006 | |

OTHER PUBLICATIONS

Rai et al. (Surgical Management for upper urinary tract transitional cell carcinoma, 2011, The Cochrane Library, Issue 4, pp. 1-20).*
Audenet et al (The role of chemotherapy in the treatment of urothelial cell carcinoma of the upper urinary tract, Sep. 29, 2010, Urologic Oncology: Seminars and Original Investigations, pp. 1-7).*
Vestraelen et al (Antiseptics and disinfectants for the treatment of bacterial vaginosis: A systematic review, 2012, BMC Infectious Diseases, vol. 12, p. 1-8).*
Szabo, HU 0102164 A2, Jun. 2003, English Abstract.*
Björn Andersch, et al; "Treatment of Bacterial Vanigosis with an Acid Cream: A Comparison between the Effect of Lactate-Gel and Metronidazole", Gynecologic and Obstretric Investigation, vol. 21(1), pp. 19-25; Issue release date: 1986.
François Audenet, M.D., et al; "The role of chemotherapy in the treatment of urothelial cell carcinoma of the upper urinary tract (UUT-UCC)", Urologic Oncology: Seminars and Original Investigations; May 2013; vol. 31(4); pp. 407-413; Epub Sep. 29, 2010.
A. Joan P. Boeke, et al; "Effect of lactic acid suppositories compared with oral metronidazole and placebo in bacterial vaginosis: a randomised clinical trial", Genitourin Med. vol. 69, pp. 388-392; Oct. 1993.
Emma J. Crosbie, et al; "Human papillomavirus as a target for manaoement, prevention and therapy", Int J Hyperthermia, Sep. 2012; vol 28(6): pp. 478-488; Epub Jun. 12, 2012.
S S El-Din, et al; "An investigation into the pathogenesis of vulvo-vaginal candidosis", Sex Transm Infect., vol. 77, pp. 179-183; Jun. 2001.
BP Rai, et al; Surgical management for upper urinary tract transitional cell carcinoma (Review); Published in The Cochrane Library, Issue 4, 2011; 22 pages.
Hans Verstraelen, et al; "Antiseptics and disinfectants for the treatment of bacterial vaginosis: A systematic review", BMC Infectious Disease; vol. 12, Dec. 2012; pp. 1-8.
International Search Report; dated Jul. 24, 2009; PCT/EP2009/056818.
Fourth Chinese Office Action dated Mar. 5, 2014; Appln. No. 200980119860.4.
USPTO RR dated Aug. 24, 2012 in connection with U.S. Appl. No. 12/996,247.
USPTO NFOA dated Mar. 14, 2013 in connection with U.S. Appl. No. 12/996,247.
USPTO FOA dated Sep. 10, 2013 in connection with U.S. Appl. No. 12/996,247.
USPTO NFOA dated Jan. 22, 2014 in connection with U.S. Appl. No. 12/996,247.
USPTO NOA dated Jun. 27, 2014 in connection with U.S. Appl. No. 12/996,247.

* cited by examiner

*Primary Examiner* — Mark V Stevens
(74) *Attorney, Agent, or Firm* — Ladas & Parry LLP

(57) ABSTRACT

The present invention relates to a vaginal suppository comprising an inert vehicle and lactic acid or a salt thereof for the treatment and/or prophylaxis of disorders in the urogenital tract.
It also relates to the use of such a suppository for the production of a medicament for the treatment and/or prophylaxis of disorders in the urogenital tract as well as to a method for the treatment and/or prophylaxis of disorders in the urogenital tract.

9 Claims, 1 Drawing Sheet

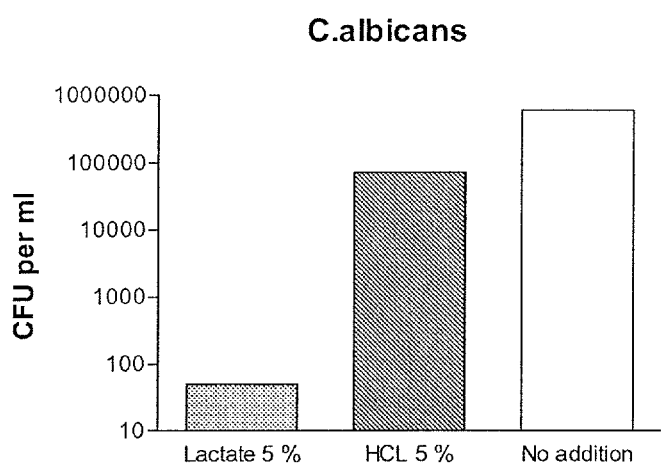
Fungicidal effect of lactate or HCL diluted in bactopeptone on *C.albicans* after 2 h of incubation at 37C. The concentration of yeast cells was analysed by viable counts. The pH was adjusted to 3.8 in the acidic solutions.

VAGINAL SUPPOSITORY COMPRISING LACTIC ACID

TECHNICAL FIELD

The present invention relates to a vaginal suppository comprising an inert vehicle and lactic acid or a salt thereof for the treatment and/or prophylaxis of disorders in the urogenital tract.

It also relates to the use of such a suppository for the production of a medicament for the treatment and/or prophylaxis of disorders in the urogenital tract as well as to a method for the treatment and/or prophylaxis of disorders in the urogenital tract.

TECHNICAL BACKGROUND

The vaginal ecosystem is a finely balanced environment maintained by a complex interaction among a variety of bacteria, infrequently including yeasts, which all occur naturally in the vagina.

Urogenital infections, including urinary tract infections (UTI), bacterial vaginosis (BV) and yeast vaginitis are common disorders in women all around the world. More than 75% of women will have at least one vaginal infection in their lives, and 50% of these women will have a recurrence of the infection.

Bacterial vaginosis generally shows little or no inflammation of the vaginal epithelium and resembles more of an alteration of the bacterial vaginal environment than a proper infection of tissues or epithelium. BV is currently treated mainly with antibiotics. Antibiotics, however, also kill useful bacteria present in the vaginal environment, such as *Lactobacilli*, resulting in a pH increase in the vaginal environment and increasing the risk of recurrence of the bacterial vaginosis or the development of a different vaginal infection, such as a yeast infection The yeast *Candida albicans* is present in most humans as a harmless commensal organism, but may cause infections, e.g. candidiasis when a person experiences a loss of normal bacterial flora. In severely immune compromised patients, *Candida albicans* can spread throughout the body and cause deadly systemic infections.

Certain *Lactobacillus* species are the dominant bacteria in a healthy vaginal ecosystem, and they maintain an acidic environment of the vagina through the production of lactic acid.

Acidity is believed to be one of the protective mechanisms of the vagina. This acidity has been associated with a decreased risk of infections such as chlamydia, genital mycoplasma, trichomoniasis, urinary tract infection and a decreased carriage of bacteria in the introitus (Hanna, N et al 1985, 1975, Stamey T A and Kaufman M F 1975, Stamey T A and Timothy M M 1975).

A favourable environment for the lactate producing microbiota is generally present, and results in a pH of approximately 4 in the mucousal secretions. However, the environment can be disturbed by factors such as variations in the oestrogen concentration during certain periods of the menstrual cycle and during the menopause, and also by an increasing occurrence of secretions of various types, for example from protracted menstrual haemorrhages, premenstrual bloody discharges, mid-cycle bleeding and ejaculate. Foreign bodies in the vagina, for example coils, pessaries and those inserted, for example, in connection with antibiotic treatment and on washing can also lead to a disruption of the healthy microbiota which is such that the pH rises. When the pH rises above 4.5 there is an increased tendency towards growth of anaerobic bacteria.

Bacterial vaginosis is an indication that the defence against infection, which is partly conferred by a low pH, has been weakened and, under unfavourable circumstances, this leads to actual infection.

Shifts in bacterial biota are associated with shifts in vaginal pH (Caillouette J C et al 1997). During BV a shift from being lactobacillus dominated to a biota in which *G. vaginalis* and anaerobic bacteria predominate is observed. The presence of anaerobic bacteria gives rise to volatile amines at an increased pH (<4.5).

An acidic envirornent is mantained by a *Lactobacillus flora* which produces lactic acid. In order for this production of lactic acid to be maintained, several attempts have been made to provide a pH reduction to create a favourable environment necessary for protection against infection.

For example, EP 0 257 007 relates to an agent for reinforcing the natural protection mechanisms of the vaginal mucosa by helping to re-establish the productive environment for lactobacteria. The agent comprises lactic acid and a buffering substance in a content such that the pH lies within the range from 3.5 to 4.

A pH below 4 makes it easier for lactobacillus species to recolonize the vagina and thereby restore the natural resistance toward overgrowth by bacteria connected with BV.

EP 1 782 794 relates to an anhydrous composition and to a method of maintaining a healthy vaginal pH to control vaginal odor. The composition may be applied to the vaginal area to lower vaginal pH and assist in maintaining such pH over a period of time.

WO 06/001766 relates to a composition comprising lactic acid and lactoferrin and/or a peptide fragment thereof for the treatment and/or prophylaxis of conditions in the urogenital tract. The incorporation of lactoferrin or a peptide fragment thereof is proposed to enhance the antimicrobial activity of the composition.

Lactate given in a gel has shown to be effective against bad odour associated with BV (Lactal). The lactate gel has also been shown to have some antibacterial effects against certain BV-associated bacterial species. (see Andersch B et al; Treatment of Bacterial vaginosis with an Acid cream: A comparison between the effect of Lactate gel and Metronidazole" Gynecol Obstet Invest 21:1925, 1986).

The lactic acid in the gel lowers the pH level and is effective in preventing malodour which appears during By.

However, application in the form of a gel is often associated with leakage from the vagina which often requires the use of some form of sanitary protection. This has an impact on patient acceptability and compliance with therapy.

Accordingly, there is a need in the art to find a more efficient local vaginal therapy for treating and/or preventing bacterial vaginosis and/or fungal infections, particularly yeast infections. Ideally, this treatment should be well tolerated, good to handle as well as provide excellent patients' acceptability.

SUMMARY OF THE INVENTION

An aim of the present invention is to provide a local vaginal therapy for the treatment of urogenital disorders being effective against bacterial vaginosis and fungal infection, in particular fungal infections caused by yeast species. The therapy should be easy, convenient and comfortable to administer and provide excellent patients' acceptability This aim is achieved by a vaginal suppository comprising an inert vehicle and lactic acid or a salt thereof, wherein the suppository comprises lactic acid or a salt thereof in a concentration of 9-15% by weight.

The present inventors have found that a vaginal suppository having a concentration of lactic acid or a salt thereof in the range of 9 to 15% by weight not only reduces malodour and creates a favourable acid environment in the vagina, but also is microbicidal against Gramnegative and Grampositive bacteria and the yeast *Candida albicans*. This is not only due to low pH, but also to the lactate molecule itself.

Typically, the vaginal suppository comprises lactic acid or a salt thereof in a concentration of 11-15% by weight, more preferably 13-15% by weight. These concentration intervals have been shown to be particularly effective for killing undesired bacteria in the urogenital tract, e.g. pathogens such as *E.coli*, GBS and *C. albicans*.

The suppository according to the invention is conveniently administered in the vagina and provides excellent patients' acceptability.

In embodiments of the invention, the inert vehicle comprises polyethylene glycol (PEG).

The inert vehicle enables the fabrication of a suppository which is relatively solid at room temperature and in a dry environment, but which melts at body temperature and in contact with body fluids. Accordingly, the active agent, i.e. the lactic acid or a salt thereof is brought in contact with the vaginal tissue upon administration.

Polyethylene glycol (PEG) gradually melts in the vaginal environment.

In alternative embodiments, the vaginal suppository may further comprise a neutralizing substance.

Such a substance is used to buffer the pH of the lactic acid,

Preferably, the content of lactic acid and neutralizing substance is such that the pH lies within the range from 3.5 to 4.5, preferably close to 3.8. The pH should not be too low since the acid may irritate the vaginal tissue or impair the environment for probiotic lactobacilli requiring a moderately acid environment.

Examples of suitable neutralizing substances include sodium hydroxide.

In another aspect, the present invention relates to the use of a vaginal suppository for the production of a medicament for the prophylaxis and/or treatment of a disorder in the urogenital tract.

The medicament has an antimicrobial activity.

A disorder in the urogenital tract typically involves an elevated pH and/or a disturbed microbiota.

Typically, the disorder is selected from the group consisting of bacterial vaginosis, intermediate vaginal microbiota, and yeast infections.

In yet another aspect, the invention relates to a vaginal suppository having the above mentioned characteristics for the prophylaxis and/or treatment of a disorder in the urogenital tract.

The invention further relates to a method for the the prophylaxis and/or treatment of a disorder in the urogenital tract, comprising administering to a patient in need thereof a pharmaceutically effective amount of a vaginal suppository having the above mentioned characteristics.

These and other aspects of the invention will be apparent from and elucidated with reference to the embodiment(s) and examples described hereinafter.

BRIEF DESCRIPTION OF THE SEVERAL VIEWS OF THE DRAWING

FIG. 1 depicts a graph representing a beneficial effect in accordance with this disclosure.

DETAILED DESCRIPTION OF THE INVENTION

It is of great importance to maintain the balance between the microorganisms in the vagina. In the treatment of vaginal infections it is important to re-establish the lactobacillus-dominated biota.

In the research work leading to the present invention, it was found that surprisingly good effects were obtained when the concentration of lactic acid or a salt thereof in a vaginal suppository was in the range of 5.5 to 15% by weight.

The vaginal suppository according to the present invention reinforces the natural protection mechanisms of the vaginal mucosa by helping to re-establish the productive environment for lactobacilli, lowering the pH and also by exerting an antimicrobial activity on a number of undesired microbes, e.g. *C. aibicans, E. coli, S. aureus, G. vaginalis*, and *Prevotella* species.

A suppository according to the invention is easy, convenient and comfortable to administer.

By "vaginal suppository" is meant a vaginal ovule, a vaginal tablet or a vaginal capsule.

The term "lactic acid or a salt thereof" means that the suppository may comprise lactic acid or a salt of lactic acid; i.e. lactate.

The concentration of lactic acid or a salt thereof should be in the range of 5.5 to 15% by weight, especially 9 to 15% by weight.

In this concentration interval several undesired bacteria present in the urogenital tract are killed.

If the concentration of lactic acid becomes too high, the subject to which the suppository is administered might experience undesired symptoms, such as a burning feeling.

The preferred concentration of lactic acid or a salt thereof is in the range of from 11 to 15% by weight, e.g. from 13 to 15% by weight. An effective killing of pathogens such as *E. coli*, GBS and *C. albicans* has been observed in this concentration interval.

The vaginal suppository according to the invention comprises an inert vehicle.

As used herein the term "inert vehicle" refers to a vehicle which brings the active substance, in this case lactic acid or a salt thereof in contact with the vaginal tissue.

The inert vehicle enables the fabrication of a suppository which is relatively solid at room temperature and in a dry environment, but which melts at body temperature and in contact with body fluids.

Any inert vehicle which has the above characteristics may be used, but typically polyethylene glycol (PEG) is used.

In embodiments of the invention, the inert vehicle comprises polyethylene glycol 600 and polyethylene glycol 4000. The ratio between PEG 600 and PEG 4000 may be varied which allows for the dissolution time of the vaginal suppositories to be varied. The properties of the inert vehicle determines the dissolution time of the vaginal suppositories in the vagina.

The vaginal suppository according to the invention may further comprise a neutralizing substance.

As used herein, the term "neutralizing substance" refers to a substance for buffering the pH of the lactic acid. Examples of neutralizing substances include sodium hydroxide and ammonia.

Preferably, the content of lactic acid and neutralizing substance is such that the pH lies within the range from 3.5 to 4.5, preferably close to 3.8. The pH should not be too low since the acid may irritate the vaginal tissue or impair the environment for probiotic lactobacilli requiring a moderately acid environment. A pH of 3.7-3.9 has been shown to be particularly advantageous.

The vaginal suppository may also comprise a growth substrate for lactic acid bacillus species.

Together with a growth substrate, the lactic acid or a salt thereof creates an ideal environment for the continued growth of lactobacteria.

The growth substrate may be α(1-4) glucans containing α(1-6) branches. An example of a suitable growth substrate is glycogen, which is found in abundance in the vaginal epithelial cells in fertile women and is an important nutrient substrate for lactobacilli. Glycogen is used as the growth substrate for the lactobacilli, so that the treatment not only results in adjustment of the pH level to a lower figure by means of supplying lactic acid, but also to re-establishment of an advantageous environment for the growth of the lactobacilli in order to regenerate the natural conditions.

Other examples of growth substrates are lactose, dextrose, glucose, and amylopectin.

Lactic acid is incorporated in a considerably greater weight proportion than the growth substrate, for example in weight ratios of 20:1 to 100:1, in particular 80:1.

The vaginal suppository of the invention may also comprise a consistency agent which provides for a suitable consistency of the suppository which is to be administered vaginally.

Additional substances, such as adjuvants, carriers, preservatives, vitamins, minerals, oestrogen etc may also be added and these substances are well known to persons skilled in the art.

The present invention further relates to the use of a vaginal suppository for the production of a medicament for the prophylaxis and/or treatment of a disorder in the urogenital tract. It also relates to a vaginal suppository for the prophylaxis and/or treatment of a disorder in the urogenital tract and to a method for the the prophylaxis and/or treatment of a disorder in the urogenital tract, comprising administering to a patient in need thereof a pharmaceutically effective amount of a vaginal suppository having the above mentioned characteristics.

By a "disorder in the urogenital tract" is meant any disturbance or disorder in the urinary tract or in the genital organs in a female and/or male. In particular, the invention is suited for the treatment of conditions in the vagina.

By "prophylaxis and/or treatment of a disorder" is meant any treatment in order to cure or alleviate a disorder according to the above, or to prevent the development of such a disorder.

By a "pharmaceutically effective amount" is meant an amount of the vaginal suppository according to the invention, which will lead to the desired pharmacological and/or therapeutic effect. The desired pharmacological and/or therapeutic effect is, as stated above, to cure or alleviate and/or prevent the development of disorders in the urogenital tract.

By a "patient" is meant any human or non-human mammal, female or male, in need of being treated with the vaginal suppository and/or method according to the invention.

The vaginal suppository has an antimicrobial activity. A very good antimicrobial activity is observed at a lactate concentration in the range of 5.5% to 15% by weight, especially in the range of 9 to 15% by weight. The antimicrobial activity is associated with the lactic acid or a salt thereof. The lactate in the suppository not only reduces the vaginal pH to create a favourable environment for Lactobacillus, but is also antimicrobial itself, By an "antimicrobial activity" is meant a bacteriostatic, fungistatic, bactericidal and/or fungicidal activity, i.e. the ability to retard the growth of and kill certain bacteria and fungi, respectively.

A disorder to be treated according to the invention may involve an elevated pH and/or a disturbed microbiota in the urogenital tract. By an "elevated pH" is meant a pH above 4.5.

By a "disturbed microbiota" is meant a biota having abnormally high levels of BV-associated bacteria, such as *G. vaginalis,* anaerobic gram-negative bacteria (*Prevotella-, Bacteroides-,* and *Fusobacterium* species), anaerobic gram-positive cocci, *Mobiluncus* species, and/or abnormally high levels of *E. coli,* staphylococci (*S. aureus*), and streptococci, all in combination with abnormally low levels of lactobacilli. Also high levels of *Candida,* which may result in vaginitis are considered a disturbed vaginal microbiota.

By an "abnormally high level" is meant a level which is 100 to 1000 fold higher than the level in a normal person.

By an "abnormally low level" is meant not predominating, i.e. not present or less than one lactobacillus morphotype per microscopical immersion field, or less or equal to other morphotypes per immersion field. (Assessment according to the "Nugent scoring system", used internationally to describe bacterial imbalance in vaginal secretion. See Nugent RP et al 1991, *J Clin Microbioi* 29:297-301.)

Examples of disorders to be treated with the vaginal suppository according to the invention are bacterial vaginosis, intermediate vaginal microbiota, and yeast infections, e.g. *Candida*-infections (*Candida vaginitis, Candida balanitis*).

Further, the vaginal suppository according to the invention may be used in the treatment of chlamydia, genital mycoplasma, trichomoniasis, urinary tract infection, pelvic inflammatory disease, HIV, gonococci and infections caused by human papillomavirus (HPV). In addition, any combinations of the aforementioned disorders may be treated with the vaginal suppository according the invention.

The vaginal suppository according to the invention may also be used e.g. in the treatment of fungal eczema, ulcerous nipples, as a prophylaxis against sexually transmitted diseases, or as a glidant.

Furthermore, it is possible to combine the vaginal suppository according to the invention with other conventional pharmacological treatments of disorders in the urogenital tract, e.g. the treatment with antibiotics and/or antimycotics, such as imidazol preparations.

Specific examples of a vaginal suppository according to the present invention emerges from the following exemplary composition:

TABLE 1

Constituents of a vaginal suppository according to the invention

| | |
|---|---|
| Lactic acid | 0.250 g |
| NaOH | 0.022 g |
| Glycogen | 0.003 g |
| PEG 4000 | 0.950 g |
| PEG 600 | 0.650 g |
| Total mass | 1.875 g |

EXAMPLE

Example 1

Antimicrobial Activity of Lactate

Bacterial Species

*E.coli* O6K5 (a urinary tract infection pathogen), a group B *Streptococcus* strain (GBS) CCUG 49086, and *C.albicans* ATCC 64549, The microorganisms were incubated over night in BHI medium. Thereafter the suspensions were transferred to new tubes and incubated for 2.5 h at 37° C. The cells were washed and suspended in diluted BHI ($\frac{1}{100}$, $BHI_{dil}$). The suspensions were measured spectrophotometrically at 590 nm and the concentrations of the microrganisms adjusted according to standard curves. The bacterial suspensions were adjusted to $2\times10^8$ CFU per ml and *C.albicans* to $1\times10^8$.

Lactate Suppositories

One lactate suppository was dissolved in 0.5 ml of distilled water. A lactate solution of 11.5% was obtained. This solution was used in the microbicidal assay.

Minimum Microbicidal Concentration of Lactate

The lactate solution was serially diluted in $BHI_{dil}$ by twofold steps in tubes (100 μl piper tube). The bacterial and yeast cell solutions were added in 10 μl volumes to give a final concentration of approximately $2\times10^7$ and $1\times10^5$ cells per ml respectively. The tubes were incubated at 37° C. on a shaker for 2.5 h. Five ul were taken from each tube and added as a drop (in triplicate) onto a blood agar plate and incubated over night at 37° C. The killing was expressed as remaining colony forming units (CFU) in relation to the inoculum. The lower limit for detection of microorganisms was 200 CFU/ml. The viability of any remaining microorganism in the tubes was checked by diluting the remaining solutions to ⅕ with growth medium, resulting in a 2.3% lactate solution or less, and incubation of the tubes over night at 37 C. The next day, once again 5 μl of the solutions were applied as drops onto blood agar plates and incubated at 37° C. over night.

TABLE 2

Microbicidal effects of lactate against
*E. coli*, GBS and *C. albicans*.

| Pathogen | Remaining viability Lactate concentration, %: | | | | | | |
|---|---|---|---|---|---|---|---|
| | 11.5 | 5.8 | 2.9 | 1.4 | 0.7 | 0.35 | 0 |
| *E. coli* | 0 | 0 | 0 | 0 | 0 | 0 | +[#] |
| GBS | 0 | 0 | + | + | + | + | + |
| *C. albicans* | 0 | 0.6 ± 0.4[□] | + | + | + | + | + |

[#]no distinguishable colonies (>50 CFU per area = >$10^4$ CFU per ml).
[□]percentage of the inoculum Results After 2.5 h of incubation, GBS was killed to 100% by the lactate concentrations 5.8 and 11.5%.

*C.albicans* was killed to 100% at 11.5% of lactate and to 99.4% at 5.8% of lactate. In contrast *E.coli* was killed to 100% by even the lowest concentration of lactate tested (0.35%).

The over night incubation of the tubes with added growth medium gave rise to the same pattern as described for the 2.5 h incubation.

FIG. 1 depicts a graph representing the beneficial effect of lactic acid at reducing viable colony forming units of C. albicans following incubation at 37 C for two hours, compared with HCl at the same concentration and pH or a control. The significantly lower CFU for the lactate treated sample (<100CFU) vs 100,000CFU when treated with HCl and 1,000,000CFU in the control, indicates the impact of a 5% lactate solution at pH 3.8 to neutralise *C. albicans*.

Comparing the fungicidal effect of lactate with HCL at identical pH showed that lactate was by far more effective in killing *C.albicans* than HCl (FIG. 1).

Conclusion

A lactate concentration of ≥5.8% effectively killed potential pathogens such as *E.coli*, GBS and *C.albicans*.

The microbicidal activity was due to both the low pH but also to the lactate molecule itself.

Example 2

Tests on Antimicrobial Effect of Lactic Acid at Different Concentrations

The aim of the present study was limited to demonstrate the antimicrobial effect of lactic acid on two microbial strains: *Candida albicans* and *Escherichia coli*, and evaluate the effect of increasing the concentration up to 14-15%. The conditions simulated the vaginal environment by adjusting the pH to 3.8 and the temperature to 35-37° C. The test aimed at adding a challenge of the test strains to containers with lactic acid in different concentrations, and incubate them at 35-37° C. in an incubator. At specified intervals samples were taken and surviving microorganisms were enumerated. Besides the test solutions controls were used in parallel. For both strains containers with 0.9% NaCl were inoculated to the same level, and tested at the specified interval. The purpose of this control was to verify that the strain is viable during the whole test. A second control was used only for *Candida*, in which a solution of HCl was adjusted to pH 3.8 with NaOH, inoculated, incubated and tested at each occasion. The exposure time for the two strains were estimated based on a pre-test made on *Candida albicans*, in 8% lactic acid, and on previous trials with lactate at this laboratory, where *E coli* had been tested in 2,5 and 5% lactic acid.

Study outline

Cultures and Solutions

*Candida albicans* ATCC 64549 and *Escherichia coli* ATCC 8739 were chosen as representing commonly isolated strains in yeast infections and bacterial vaginosis. The strains were inoculated on Sabouraud Dextrose agar (SDA) and Tryptone Soya agar (ISA) plates respectively, at 35-37° C. for 18-24 hours. The surface growth was harvested, rinsed and the suspensions were diluted to a defined optical density. The titer was determined by measuring the absorbance at 540 nm.

L(+)-Lactic acid from Purac Biochem was supplied by Kullgren Pharma, Gnesta, Sweden, as a 90% concentrate solution. This was diluted to 5, 8 and 14.5% v/v , adjusted by addition of NaOH to pH 3.8, sterile filtered and added to test containers. Other containers contained controls, sterile 0.9% NaCl pH 7 and HCl pH 3.8. The solutions were then preconditioned to 35-37° C. in the incubator before adding the challenge and starting the exposure.

Exposure Testing

The containers were challenged with $10^5$-$10^6$ cells per ml, and the incubation was started. For the *E. coli* test samples were taken at 0, 10, 20, 60 and 240 minutes. For *C. albicans* samples were taken at 0 h, 6 h and 24 h. Dilutions were made according to a detailed protocol, samples were drawn from the test containers and filtered through 0.45 μm filters. The filters were rinsed with 3 portions of 100 ml 0.9% NaCl and then placed onto agar plates, TSA and SDA respectively. Single samples were used throughout.

Method Validation:

Since the method validation for the pre-test had shown that aliquots of lactic acid up to a concentration of 8% could be filtered and rinsed as described, without inhibiting the growth on the plated filters, it was decided to perform such validations with the highest concentration, 14.5%, with both strains, directly in parallel with the test, for both strains. For this purpose a sterile sample of 14.5% pH 3.8 lactic acid was filtered, the filter was rinsed and 10-100 CFU of the test strain was included in the final rinse. A second filter without lactate treatment was rinsed in parallel, plated and both plates were incubated. The numbers of resulting CFU on the two plates must match within 50-200% for the method to be valid. This was repeated for both strains. The results for both strains fulfilled the acceptance criterion (data not shown).

Results and Discussion

The results are given in table 3 and 4. For *E. coli*, the inactivation is rapid, and no survivors are found after 10 minutes exposure (see table 3). At time 0, which means an exposure time of 1-2 minutes, while the sample is taken and tested, for the 5% sample there was a reduction from $4.5 \times 10^5$ (as seen in the control) to $1.3 \times 10^3$, which equals $2.6\ ^{10}\log$. The 14,5% concentration had no survivors in the 0 time sample. The control verified that the challenge organisms were viable in a neutral environment.

TABLE 3

Survival of *E coli* in lactic acid (results are presented as CFU/ml)

| Exposure time | Control 0.9% NaCl pH 7 | 5% lactic acid | 14.5% lactic acid |
|---|---|---|---|
| 0 min | $4.5 \times 10^5$ | $1.3 \times 10^3$ | 0 |
| 10 min | $5.0 \times 10^5$ | 0 | 0 |
| 20 min | $3.7 \times 10^5$ | 0 | 0 |
| 60 min | $3.5 \times 10^5$ | 0 | 0 |
| 240 min | $2.0 \times 10^5$ | 0 | 0 |

TABLE 4

Survival of *C albicans* in lactic acid (results are presented as CFU/ml)

| Exposure time | Control 0.9% NaCl pH 7 | Control HCl pH 3.8 | 8% lactic acid | 14.5% lactic acid |
|---|---|---|---|---|
| 0 h | $3.3 \times 10^5$ | $2.9 \times 10^5$ | $3.6 \times 10^5$ | $1.8 \times 10^5$ |
| 6 h | $3.1 \times 10^5$ | $3.4 \times 10^5$ | $8.4 \times 10^4$ | 1 |
| 24 h | $2.4 \times 10^5$ | $2.0 \times 10^5$ | $9.8 \times 10^3$ | 2 |

For *Candida albicans* the 8% sample showed a reduction after 6 hours of 0.6 logs, and after 24 hours 2.2 logs; i.e. a reduction by 97.2%

For the 14.5% sample there was a 5.3 log reduction already after 6 hours; i.e. a reduction by >99.999%. The controls verified that the cells were viable in a neutral environment, and that the reduction was not caused by the pH reduction to 3.8, but to the lactic acid itself.

Conclusion

It has been shown in a limited test, that lactic acid has a very rapid antimicrobial effect on *E coli* at both concentrations tested, but that it has a much more rapid effect at 14.5% than at 5%. Similarly, lactic acid at 8% has also a verified antifungal effect on Candida albicans, seen both at the 6 hour test, and at the 24 hour test. The 14, 5% concentration shows a much more rapid reduction, and within 6 hours the challenge is reduced to practically nil.

Example 3

Treatment of Abnormal Vaginal Discharge: A Comparative Study on the Effects with Vaginal Suppositories and Vaginal Creams Study Outline Thirty patients complaining of an abnormal vaginal discharge received treatment with vaginal suppositories in one single intravaginal dose applied nightly before sleeping, for seven days.

During treatment the women were told to avoid taking any other medication or using intravaginally hygien products. The second visit took place after one week treatment.

Vaginal suppository

The composition of the vaginal suppository administered was as illustrated in Table 1 above. The concentration of lactic acid was 13% by weight and the pH was 3.8.

Lactal Gel

The composition of the lactal gel was as follows:

| | |
|---|---|
| Lactic acid | 5.0 g |
| NaOH for buffering the lactic acid to a pH of 3.8 | 4.1 g |
| Glycogen | 0.1 g |
| Propylen glycol (85%, remainder H2O) | 15 g |
| Consistency agent such as methyl hydroxypropyl ether of cellulose giving a gel form | 100 g |

The concentration of lactic acid was 5% by weight.

Laboratory Tests and Questionnaires

1. Amine Test/Whiff Test

After removal of the speculum, a small amount of 10% potassium hydroxide (KOH) was dripped on the speculum where some secretion was always found. A rotten fishy odour was recorded as positive.

2. pH measurements

Vaginal discharge collected was scraped off to a paper (Merck, Darmstadt, Germany) and read in comparison to the standard reading provided by the manufacturer.

3. Wet Smear

Vaginal fluid was collected from posterior fornix and mixed with normal saline for microscopic examination. Clue cells were identified as vaginal epithelial cells with adherent bacteria which obscured the cell border.

4. Acceptability

Acceptability was evaluated by the patients on a questionnaire at the control visit. The acceptability was evaluated as excellent, good or null.

5. Tolerance or adverse effects were evaluated by the patient on a questionnaire.

6. The diagnosis of By was made if the patient's discharge fulfilled all three of the following criteria (Amsel criteria (1)); (A) pH>4.5, (B) Positive amine test, (C) The presence of clue cells in the wet smear.

Results
pH-measurements

| Measurements done by the doctor | pH < 4.5 N | pH > 4.5 N |
|---|---|---|
| Before using the Lactal suppositories | 0 | 30 |
| After using the Lactal suppositories | 30 | 0 |

Amine/Whiff Test
Positive Test in Percent

| Day 1 | Day 7 |
|---|---|
| 100% | 0% |

Clue Cells

| Day 1 | Day 7 |
|---|---|
| 100% | 0% |

The Number of Improved Women Treated with Lactal Gel Compared to Vaginal Suppositories.
Women who lacked all Amsels three criteria were clinically improved.

| Amsels criteria | Clinically improved | Not clinically improved |
|---|---|---|
| Lactal Gel (7) | 24 | 7 |
| Lactal Suppositories | 30 | 0 |

Fisher's exact test, Two-sided
P value = 0.0107

Improvement of Malodour

Thirty women (100%) assessed no smell on day seven. In 27 women the odour disappeared already after one day treatment. None of the women experienced the odour worsening during the study period.

Acceptability

The acceptability of the local treatment was analysed by the patients and 28 women (93%) judged the acceptance of the treatment as excellent and two women as good. 27(90%) women had to use panty liners during the treatment period. 25 women would prefer the vaginal suppositories over the Lactal gel.

Tolerance or Adverse Effects

The tolerance evaluated by the doctor and by the patients allowed for the detection of adverse effects in only one woman. She complained of slight burning feelings and could continue the treatment all days.

Conclusion

Patient acceptability and preference are important aspects of local vaginal therapy. The treatment should be easy, convenient and comfortable to administer. The present study confirms that the use of the vaginal suppositories is well tolerated, good to handle and receives excellent patients' acceptability. The women experienced both ease and comfort to administer the suppositories. The suppositories are individually packed giving a high hygienic standard. The excellent patient acceptance of the vaginal suppositories could result in improved medication compliance and more consistent treatment of BV.

Thirty patients have been treated with vaginal suppositories and no significant adverse drug reactions were reported. Only one patient complained of slight burning reaction but was able to continue the treatment.

Despite the limited number of patients in this study it would appear that the use of the vaginal suppositories could be of particular interest in treating women with BV. We observed that all women were clinically improved concerning the symptom of malodour and that the pH level in the vaginal secretion decreased below 4.5 and no clue cells were found.

Thus, vaginal suppositories have been shown to be safe and effective in the restoration of a normal vaginal pH following a 7 day treatment regimen. We showed that the vaginal suppositories compared to Lactal gel (7) were significantly more effective according to Amsels criteria in treating women with BV. The lactate concentration in the suppositories is higher than Lactal gel and the clinically effect is not only exerted by its low pH but also by lactate itself. We have found that lactate is more effective than HCl against microbial species and more potent in higher concentration (6).

The product was excellent tolerated and very well received and therefore merits a place among the therapeutic arsenal for these vaginal ecosystem alterations.

REFERENCES

1. Andersch B, Brandberg A, Hoist E. The treatment of bacterial vaginosis—an acidifying gel instead of antibiotic therapy-Läkartidningen 1998;87:465-468
2. Gine L, Lopez Castejon A, Julia E, Carreras R, Balaguero L New therapeutic techniques. Use of a lactic acid and glycogen gel in vaginitis. Clinical Study. Toko Ginecologia Practica 2001;60:337-386
3. Massimo B and Andersch B Etude clinique multicentrique pour evaluer le'fficacite de Geliofil gel Rapport de'ssai Effik. Unpublished data 1996:1-2
4. Andersch B Agent for treating conditions in the vagina EPO 257007A1, 1988
5. Mead, Philip B, Epidemiology of Bacterial vaginosis. Am J of Obstet and Gynecol 1993;169:446-449
6. Mattsby-Baltzer I manuscript 2008
7. Andersch B Forssman L, Lincoln K, Torstensson P, Treatment of Bacterial Vaginosis with an Acid Cream:A Comparison between the Effect of Lactate-Gel and Metronidazole Gynecol obstet Invest 1986,21:19-25

The invention claimed is:

1. A composition consisting essentially of an inert vehicle and lactic acid or lactate, wherein the concentration provided by the lactic acid or lactate is 11-15% by weight, and wherein the composition is formulated as a vaginal suppository.

2. A composition according to claim 1, wherein the concentration provided by the lactic acid or lactate is 13-15% by weight.

3. A composition according to claim 1, wherein said inert vehicle comprises polyethylene glycol (PEG).

4. A composition according to claim 1, further comprising a neutralizing substance.

5. A composition according to claim 4, wherein the content of lactic acid and neutralizing substance is such that the pH lies within a range of 3.5 to 4.5.

6. A composition according to claim 4, wherein said neutralizing substance is sodium hydroxide.

7. A composition according to claim 1, wherein said suppository has an antimicrobial activity for treating vaginal bacterial and fungal infections.

8. A composition according to claim 7, wherein said vaginal bacterial and fungal infections involve an elevated pH and/or disturbed microbiota in the urogenital tract.

9. A composition according to claim 7, wherein said vaginal bacterial infection is bacterial vaginosis.

* * * * *